United States Patent [19]
Böhm et al.

[11] Patent Number: 5,817,528
[45] Date of Patent: Oct. 6, 1998

[54] STERILE AND PYROGEN-FREE COLUMNS CONTAINING COUPLED PROTEIN FOR BINDING AND REMOVAL OF SUBSTANCES FROM BLOOD

[75] Inventors: Wolfgang Böhm, Munich; Franz A. Bieber, Unterschleissheim; Jutta Müller-Derlich, Germering, all of Germany; Alan Barclay, Ophain, Belgium; Reiner Spaethe, Starnberg, Germany; Michael Bernhard, Dachau, Germany; Christine Kraus, Munich, Germany

[73] Assignee: Therasorb Medizinische Systeme GmbH, Unterschleissheim, Germany

[21] Appl. No.: 442,213

[22] Filed: May 16, 1995

Related U.S. Application Data

[63] Continuation-in-part of Ser. No. 242,215, May 13, 1994, abandoned.

[51] Int. Cl.[6] .......................... G01N 33/544; C12N 11/00; C07K 17/00; C07K 17/10

[52] U.S. Cl. .............................. 436/529; 435/2; 435/174; 435/176; 435/178; 435/180; 436/518; 436/524; 436/531; 530/402; 530/413; 530/810; 530/811; 530/813; 530/815

[58] Field of Search ................................ 435/2, 174, 176, 435/178, 180; 436/518, 524, 529, 531; 530/402, 413, 810, 811, 813, 815

[56] References Cited

U.S. PATENT DOCUMENTS

| | | | |
|---|---|---|---|
| 4,381,239 | 4/1983 | Chibata et al. | 210/679 |
| 4,424,206 | 1/1984 | Ohmura et al. | 424/101 |
| 4,560,504 | 12/1985 | Arnold | 260/112 B |
| 4,576,928 | 3/1986 | Tani et al. | 502/404 |
| 4,693,985 | 9/1987 | Degen et al. | 436/531 |
| 5,281,579 | 1/1994 | Estep | 514/6 |
| 5,328,603 | 7/1994 | Velander et al. | 210/198.2 |

*Primary Examiner*—David M. Naff
*Attorney, Agent, or Firm*—Seed and Berry LLP

[57] ABSTRACT

A method is provided for producing a sterile and pyrogen-free column containing coupled protein for use in removing a predetermined substance from the blood of a human subject. The method abrogates sterilization of the finished protein-containing product by providing sterile and pyrogen-free raw materials at each production step. The method provides a pathogen-free, purified solution of protein which binds to a predetermined substance in human blood such as LDL or immunoglobulin. Typically, the protein is anti-human LDL immunoglobulin or anti-human Ig immunoglobulin. The method also provides a sterile and pyrogen-free column matrix material such as an agarose which is chemically activated, either using CNBr and triethylamine or using 1,1'-carbonyldiimidazole. The sterile and pyrogen-free, activated matrix material and the pathogen-free, purified protein solution are combined under aseptic conditions to effect the coupling of the protein to the matrix material, and the protein-coupled matrix material is filled under aseptic conditions into a sterile and pyrogen-free housing to produce a sterile and pyrogen-free column.

20 Claims, 5 Drawing Sheets

|    |            |                    |                    |                     |
|----|------------|--------------------|--------------------|---------------------|
| 25 |            |                    |                    |                     |
| 26 |            |                    |                    |                     |
| 27 | SYMBOLS:   |                    |                    |                     |
|    | ▢          | production step within isolator | | |
|    | ▢          | bulkware, work in process-product (WIP) | | |
|    | ⬭ (hatched) | production step with SOP | ◇ | in process/release test |

*Fig. 1E*

STERILE AND PYROGEN-FREE COLUMNS CONTAINING COUPLED PROTEIN FOR BINDING AND REMOVAL OF SUBSTANCES FROM BLOOD

This a application is a continuation-in-part of application Ser. No. 08/242,215, filed May 13, 1994, now abandoned.

TECHNICAL FIELD

The invention relates generally to columns over which blood is passed to remove substances from the blood. Specifically, the invention is in the field of methods for producing sterile and pyrogen-free columns coupled to proteins which bind to and remove pre-determined substances from blood.

BACKGROUND

It has long been recognized that certain disease states are associated with the presence of an excess of specific substances in the patient's blood. For instance, in familial hypercholesterolemia (FH), the levels of low-density-lipoprotein (LDL) or lipoprotein a (Lp(a)) in the patient's blood are greatly elevated due to a genetic defect in the LDL receptor. The elevation of LDL leads to rapidly developing atherosclerosis in the patient's coronary arteries, which in turn leads to early heart attack and death.

To remove excess LDL, plasma of FH patients is passed over columns containing a matrix which is coupled to antibodies which specifically bind to and remove the LDL/cholesterol complex. This procedure is described in the following publications: Stoffel, W., et al., *Lancet* II, p. 1005–1007, 1981; Borberg, H., et al., *J. Clin Apheresis* 4:59–65, 1988; Gordon, B. R., et al., *Transfusion* 30:327–332, 1990; Borberg, H., et al, *Plasma Separation and Plasma Fractionation* pp. 266–271 (Karger, Basel 1983); Hombach, V., et al., *Deutsche Med Wochenschrift* 111:1709–1715, 1986; Borberg, H., et al., *Arztl.Lab.* 32:57–62, 1986.

Another type of LDL-removal column has been proposed to non-specifically remove cholesterol from a patient's blood (U.S. Pat. No. 4,576,928; U.S. Pat. No. 4,637,994; Liposorber®, Sulflux®, Kaneka Corporation, Osaka, Japan). The Kaneka column adsorbent consists of a water-insoluble porous hard gel on which a sulphated compound is immobilized by a covalent linkage.

It has also been proposed to remove LDL by heparin-induced extracorporeal LDL precipitation (HELP™, Braun, Melsungen, Germany).

Another need for removal of substances from a patient's blood arises in certain autoimmune and other diseases. It is generally believed that the symptoms of autoimmune diseases such as systemic lupus erythematosus (SLE), rheumatoid arthritis (RA), idiopathic thrombocytopenic purpura (ITP), Myasthenia gravis, and vasculitis, are caused by auto-antibodies and circulating immune complexes (CIC) in the patient's blood which are directed against the patient's self-antigens. Thus, it has been proposed that the removal of a large portion of the patient's immunoglobulin, including auto-antibodies and CIC, may lead to amelioration of symptoms, and possibly a cure.

Columns have been coupled to *Staphylococcus aureus* Protein A, which binds to certain subclasses of human IgG (Immunosorba®, Excorim®, Lund, Sweden). The removal of certain subclasses of IgG is currently accomplished by perfusing the recipient's plasma over these *S. aureus* Protein A-coupled columns. The Protein-A coupled columns have been proposed for use in the treatment of patients with autoimmune diseases such as Goodpasture's syndrome, Wegener's granulomatosis, and SLE (EXCORIM® manual EM-32–101-B, 1989, Lund, Sweden; Bygren, P., et al., *Lancet* December 7, p.1295–1296, 1985). The Protein-A coupled columns have also been used for the removal of anti-HLA antibodies from hypersensitized patients who are in need of a kidney transplant (Dantal, J., et al., *New England J. Med.* 550:7–14, 1994; Palmer, A., et al., *The Lancet* Jan. 7, 1989, pp.10–12). These patients typically suffer from idiopathic nephrotic syndrome (INS). They commonly suffer a relapse soon after transplantation of even the most well-matched donor kidney, thus practically excluding them from the possibility of having any kind of kidney transplant. The efficacy of the Protein A column treatment in several INS patients was reported (Dantal,et al, supra; Palmer, et al., supra). Protein-A-coupled columns were also used in the treatment of patients with antibody inhibitors to coagulation factors VIII or IX (Nilsson, I. M., et al., *Blood* 58:38–44, 1981; Gjörstrup, P., et al., *Vox. Sang.* 61:244–250, 1991).

Interferon has also been implicated as a possible pathogenic substance in the blood of patients suffering from autoimmune diseases, allergy, and rejection of transplanted tissue. It has been proposed that anti-interferon immunoglobulins coupled to a solid support could effect the removal of interferon from the blood of such patients (Skurkovich, S. V., U.S. Pat. No. 4,581,010; Skurkovich, S. V., U.S. Pat. No. 4,362,155; DE 32 39 360 C2; GB 2122496B; WO 82/03331).

It is also possible to treat certain autoimmune diseases by removal of a significant portion of the patient's immunoglobulins using a column coupled to antibodies directed against human immunoglobulin. Use of such columns in the treatment of auto-immune disease has been reported as follows: Müller-Derlich, J., et al., *Congress in Monte Carlo*, April, 1992; Müller-Derlich, J., et al., *IX. Congress of the International Society for Artificial Organs* July 1993; Müller-Derlich, J., et al., *Ninth Scientific Congress of the European Society for Haemapheresis in Association with the British Blood Transfusion Society*, September 1993; Müller-Derlich, J., et al. *XXIV. Tagung der Gesellschaft für Immunologie.*

September/October 1993; Müller-Derlich, J., et al. *Conference on Immunoglobulins Intravenous IgIV*, Lisbon, November 1993.

Another instance for removal of substances from a patient's blood arises when the patient is in need of an organ transplant. Generally, the transplanted organ must be immunologically matched to the recipient in order to prevent hyperacute rejection of the donor organ. However, there is a world-wide shortage of transplant-quality human organs, and the need to immunologically match the donor organ to the recipient further complicates the picture.

If a donor organ is transplanted against which the recipient has preformed antibodies, hyperacute rejection of the donor organ follows rapidly after transplant. Hyperacute rejection typically occurs in an allograft when the recipient has preformed antibodies against the HLA type of the donor organ (human to human) and in a xeno-graft (animal to human) because humans normally have preformed antibodies against animal tissues.

The "hyperacute rejection reaction" occurs when the recipient's own immune system attacks and destroys the transplanted organ within minutes to hours, typically within 48 hours after transplant. Even when the recipient receives immunosuppressive therapy, hyperacute rejection is not ameliorated.

The use of an organ from an animal species such as the pig will not be practical unless a method is found to greatly reduce or prevent the hyperacute rejection reaction. The hyperacute rejection reaction is thought to occur as a result of pre-formed antibodies in the blood of the recipient which recognize and bind to xeno-antigens in the tissue of the donor organ once the transplanted organ is in place and is perfused with the blood of the recipient. These preformed antibodies in the recipient's blood are also known as "human heterophile antibodies", "natural antibodies" or "xenoreactive antibodies". When the xenoreactive antibodies bind to endothelial cells of the donor organ blood vessels, they stimulate the deposition of complement proteins, which also originate from the blood of the recipient. Xenoreactive antibody/complement deposition is thought to initiate the "classical" pathway of complement action, which ultimately leads to disruption of the endothelial cell lining of the blood vessels of the donor organ (In: *Immunology*, Eds: Roitt, I. M., et al, J. B. Lippincott Co, Philadelphia, 1989, Chapter 13, pages 13.1–13.16). The hyperacute rejection reaction results in a necrotic donor organ within minutes to hours after xenotransplant. It has been hypothesized that necrosis of the donor organ results from "activation" of its endothelial cells, which in turn leads to interstitial hemorrhage, inflammation, edema, and small vessel thrombosis (Platt, J. L., et al., *Immunology Today* 11:450–456, 1990; Magee, J. C., et al., *Therapeutic Immunology* 1:45–58, 1994).

In attempts to prevent hyperacute rejection when ABO-mismatched human organs were transplanted, pre-formed anti-A/anti-B antibodies were removed from the recipients' blood using extracorporeal perfusion of the recipients' plasma over synthetic A/B blood group antigens covalently linked to silica. Successful kidney and bone marrow transplants were reported using this procedure (Bannett, A. D., et al., *Transplant. Proc.* 1987 XIX:4543–4546; Bensinger, W. I., et al., *Transplantation* 1982 33:427–429; U.S. Pat. No.: 4,137,401; European patent no: 89311540.2).

Several procedures have been proposed to remove xenoreactive antibodies from the blood of a recipient of an animal organ. For instance, the recipient's blood could be perfused through an organ of the proposed donor species prior to transplantation of a "fresh" organ. Alternatively, if a pig is to be the donor species, a "column" could be constructed of isolated pig endothelial cells, for instance. The recipient's plasma could be perfused over this column to remove anti-pig antibodies prior to transplantation. (Bach, F. H., IN: *XENOTRANSPLANTATION*, Eds: Cooper, D. K. C., et al. Springer-Verlag, 1991, Chapter 6).

It has also been proposed that antibodies be removed non-specifically from the recipient's blood prior to xenotransplantation, in the hope that xenoreactive antibodies will be removed along with the rest. Immunoglobulin can be removed non-specifically by plasmapheresis. However, conventional plasmapheresis is associated with side-effects which make it impractical for treating organ-transplant patients.

What is needed is a method to produce sterile and pyrogen-free columns coupled to specific proteins for the removal of predetermined substances from the blood of patients suffering from conditions such as elevated LDL/cholesterol, autoimmune disease, and conditions requiring transplantation of solid organs.

SUMMARY OF THE INVENTION

The invention provides a method to produce a sterile and pyrogen-free column coupled to protein which binds a predetermined substance in human blood, thereby removing that substance when the plasma of the subject is passed over the column.

The predetermined substances to be bound and removed may be, for instance low-density-lipoprotein (LDL) and Lp(a), and associated cholesterol complexes. Alternatively, the predetermined substances to be removed may be immunoglobulins such as IgG, IgM, IgA and IgE, and circulating immune complexes.

The coupled protein may be a mixture of polyclonal, monoclonal, or recombinant antibodies directed against human LDL or human immunoglobulin. The coupled antibodies may be raised in animals, or may be recombinantly produced as double-chain or single-chain antibodies. When the coupled antibodies are directed against human immunoglobulin, they can bind specifically to human IgG, IgM, IgA, IgE, or to a mix of human immunoglobulin classes.

Accordingly, it is an object of this invention to provide a method to produce a sterile and pyrogen-free column coupled to protein which binds to and thereby removes a pre-determined substance from the blood of a primate subject, including human subjects.

It is a further object of this invention to provide a method to produce a sterile and pyrogen-free column coupled to antibodies which specifically bind to and remove human LDL from the plasma of a human subject.

It is yet another object of this invention to provide a method to produce a sterile and pyrogen-free column coupled to anti-human immunoglobulin antibodies for use in removing immunoglobulin and circulating immune complexes from the plasma of primate subjects, including human subjects.

An additional object of this invention is to provide a method for large-scale production of sterile and pyrogen-free protein-coupled columns.

BRIEF DESCRIPTION OF THE FIGURE

FIGS. 1(a)–1(e) show a flow-chart of the method for producing sterile and pyrogen-free columns coupled to protein.

DETAILED DESCRIPTION OF THE INVENTION

Figure 1A:
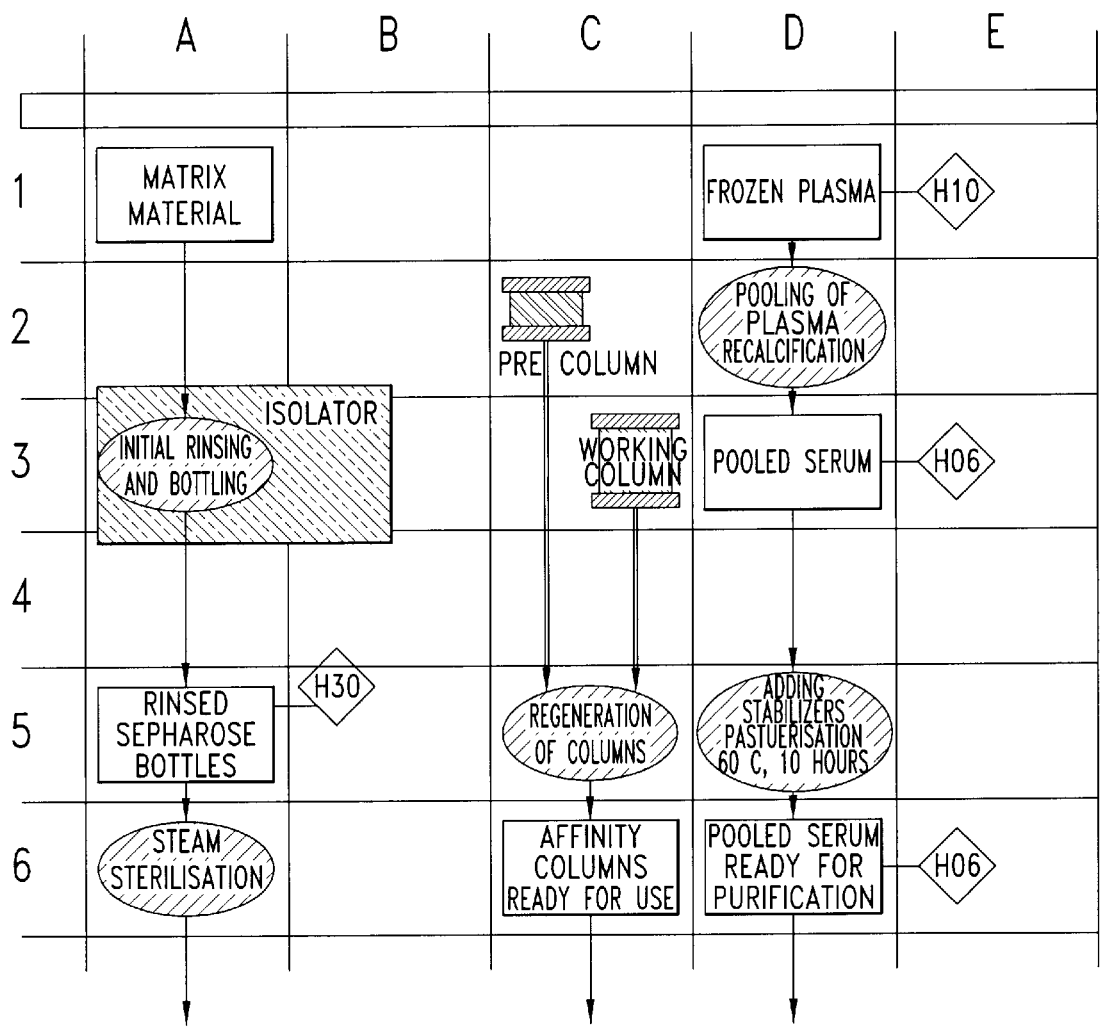

The invention provides methods to produce sterile and pyrogen-free columns coupled to protein for the removal of predetermined substances from a subject's blood. The methods are carried out under aseptic conditions, using sterile raw materials. The method of the present invention avoids the use of deleterious conventional methods for sterilization of medical products.

Herein, the term "column" is defined as a module of any shape having a matrix material to which proteins can be chemically coupled.

When a column is to be used in processing the blood of a human subject, it is understood that the column must be sterile and pyrogen-free to minimize the possibility that pathogenic substances could be returned to the subject via the column effluent. There is a major problem presented in the production of a protein-coupled, sterile and pyrogen-free column. This major problem is based on the fact that the finished therapeutic column cannot be sterilized by any practical means without destroying its function. The four conventional means for sterilizing a medical product are (1) ethylene oxide saturation; (2) glutaraldehyde saturation; (3)

gamma irradiation; and (4) steam sterilization. Ethylene oxide ($EtO_2$) sterilization would involve saturation of the final product with $EtO_2$, followed by vaporization and evacuation of $EtO_2$ gas. $EtO_2$ sterilization can only be used for solid materials, and not for products which contain fluids such as the buffer solution in the column of the present invention. Glutaraldehyde saturation would cause fixation and cross-linking of the coupled protein and thereby diminish its binding function. Gamma irradiation would be expected to disrupt the three-dimensional structure of the coupled protein and alter the column matrix material. Moreover, some countries, such as Germany, do not allow the use of gamma irradiation in the preparation of pharmaceuticals. Conventional steam sterilization at 121° C. for 15 minutes at 2×bar would melt the column matrix material, rendering it unusable for the intended purpose, and denature the coupled protein, thereby destroying its binding activity.

The method of the present invention solves the sterilization problem by utilizing sterile and pyrogen-free raw materials at each production step. The methods for providing sterile and pyrogen-free raw materials are described at each step below, and in greater detail in the experimental examples.

The protein coupled to the column can be *Staphylococcus aureus* Protein A or Streptococcus Protein G, or antibodies raised against human LDL, or antibodies raised against human immunoglobulin.

The working examples presented below are directed to columns containing matrix material having antibodies coupled thereto. Since antibodies are complex proteins which possess specific binding activities, it is expected that the same methods could be successfully applied to the production of columns coupled to Protein A or Protein G.

When the protein to be coupled to the matrix material of the column comprises antibodies, the antibodies can be polyclonal antibodies raised by well known means in animals such as sheep or rabbits. The immunogens can be human immunoglobulin (Ig) or human LDL. Alternatively, the antibodies bound to the columns may be monoclonal antibodies produced by well known means using human immunoglobulin or human LDL as the antigen. The screening procedure for choosing an appropriate monoclonal antibody against human Ig could be based on selectivity for human immunoglobulin which binds to pig endothelial cells. Once the sequence of an appropriate monoclonal antibody is determined, the antibody could be recombinantly produced as a double- or single-chain antibody.

When the antibody to be coupled to the column is raised in an animal, it is especially important to assure that any viruses present in the animal serum are inactivated. The present invention method provides methods for inactivating viruses while maintaining high levels of functional antibody. One method is heat treatment. Briefly, the animal serum is mixed with a stabilizer, heated to at least 60° to about 62° C., and held at this temperature for at least 10 hours. This antibody inactivation process was validated by studies using several types of test viruses known to mimic a range of pathogenic viruses in their susceptibility to physico-chemical inactivation. Other methods are solvent/detergent treatment and virus filtration.

Once the animal serum or other source of antibody has been validated as pathogen-free, it is preferably purified to select the appropriate antibodies destined for coupling to the therapeutic column product. Suitably, the purification step involves passage of the antibody solution over a first column, termed herein a "pre-column" containing a matrix material having albumin coupled thereto, and then over a second column, herein termed a "working column". When anti-LDL antibodies are to be purified, the matrix material of the pre-column also has human IgG as well as albumin coupled thereto.

Preferably, the working column contains a sterile and pyrogen-free matrix material having human immunoglobulin or human LDL coupled thereto under aseptic conditions. A working column with a capacity of about 450–900 ml is used.

The column matrix material is preferably sterilized by (1) a series of rinses with sterile pyrogen-free water to reduce bioburden, followed by (2) steam sterilization under conditions which will not melt the matrix material, preferably 115° C. for at least 20 minutes at <2 bar (until $F_0=6$). All sterilization procedures are carried out inside a sterilized isolator with glove boxes, placed inside a class 100,000 clean room.

Suitably, the working column for the purification of antibodies against human immunoglobulin contains matrix material having human immunoglobulin coupled thereto. Preferably, a preparation of pooled human immunoglobulin such as Gammagard®S/D (Baxter, Hyland Division) is purified to obtain human IgG, and the purified human IgG preparation is coupled to a sterile matrix by means of cyanogen bromide activation. An alternative method for coupling is provided which makes use of 1,1'-carbonyldiimidazole (CDI) as the activating agent. The activation and coupling process is also carried out inside the sterilized isolator. Alternatively, a mix of human immunoglobulins such as IgG, IgM, IgA, and IgE may be coupled to the sterile matrix.

Suitably, for the purification of antibodies against human LDL, the matrix of the working column is coupled to human LDL derived by affinity chromatography of the plasma of human subjects.

The solution of antibodies destined for coupling to the therapeutic column is then purified by passage over the pre-column to which non-desired substances bind. The eluant from the pre-column is then passed over the working column, which binds the desired antibodies while allowing undesired substances to flow out of the column. The passage over pre- and working columns is suitably carried out by an automatic system installed in a class 100,000 clean room. Sterile buffers are used for all processes.

Once the desired antibodies have bound to the working column, and the undesired substances have flowed out of the column, the desired antibodies must be eluted from the working column. There are four major hurdles presented at this step. Firstly, the desired antibodies must be eluted in sufficient quantity to make production of the therapeutic columns practical and cost-effective. Secondly, the desired antibodies must be eluted in a functional state, i.e. their binding sites must be sufficiently unaltered such that they can still bind their epitopes on human immunoglobulins or LDL. Thirdly, the resulting eluted antibody solution should not have a buffer chemical which would itself bind to the activated column matrix in the ensuing steps. Fourthly, the eluted antibodies should be stable in storage for an extended time in the elution buffer. Within the current state of the art of protein purification, these four requirements are often mutually exclusive. That is, conditions which elute a sufficient quantity of the protein may inactivate the protein (Wilchek, M, et al., IN: Methods in Enzymology, Volume 104, "Enzyme Purification and Related Techniques", Ed: W. B. Jakoby, 1984, Harcourt Brace Jovanovich, pp.19–34).

Moreover, a buffer which effectively elutes the protein may not be a suitable buffer for later processing, or it may not be conducive to the stability of the protein during storage.

Fortunately, three elution buffers were discovered that meet the above requirements. In the course of discovering a suitable elution buffer, glycine buffer was first tried because glycine is widely used for standard affinity chromatography. Since glycine is an amino acid, it contains amino groups. It was found that prior to coupling the eluted sheep antibody to the CNBr-activated column matrix, the glycine had to be removed from the antibody solution because otherwise both the antibody and the glycine molecules would be subsequently coupled to the column matrix material destined for the final product. The occupation of activated coupling sites by glycine would displace protein coupling sites, and thereby diminish the immunoglobulin or LDL binding capacity of the column. Removal of the glycine buffer required a time-consuming dialysis procedure to replace the glycine with carbonate buffer.

Next, to avoid amino groups, an acetate buffer was tried (0.10M sodium acetate/0.150M NaCl/HCl). However, it was found that the working columns lost their binding capacity over time. This was due to incomplete elution of antibody, which caused a high proportion of the binding sites on the working column to become permanently occupied. Fortuitously, two suitable citrate elution buffers were discovered, as well as a better acetate buffer. Preferred elution buffers are:

(1) 5 mM mono-sodium citrate/10 mM citric acid, pH 2.8

(2) 5 mM mono-sodium citrate/63 mM citric acid, pH 2.2

(3) 5 mM sodium-acetate/acetic acid, pH 2.8 The elution buffer is passed over the working column coupled to antibodies, and eluted antibodies are passed through sterilizing filters on-line.

Preferably, a working column with a capacity of about 450–900 ml is used. After 3,000–8,000 ml of elution buffer have been passed over the working column, the collected eluate contains 70–100% of the antibodies originally bound to the column.

The collected anti-human Ig or anti-human LDL antibodies are then coupled to a sterile matrix material under sterile conditions. Preferably, the matrix material is a carbohydrate-based material such as Sepharose™. Other suitable matrix materials include autoclavable matrices such as beads, fibers, and membranes composed of glass or synthetic polymers such as polymethacrylates, polystyrenes, and polyamides.

The coupling procedure is carried out in a sterilized isolator with glove boxes (class 100) placed in a class 100,000 clean room. The inner parts of the isolators are sterilized by the use of a special ultrasonic gas nebulization process using peracetic acid and hydrogen-peroxide in acetic acid. All materials entering or leaving the isolators are sterile, or are destined to be sterile filtered.

In order to conduct the coupling procedure on a practical scale, a large stainless steel activation vessel is used to activate 1800 ml sepharose in one batch within an isolator. Preferably, the stainless steel vessel is sterilized by gas nebulization in the isolator. Alternatively, the stainless steel vessel may be heat sterilized a 250° C. for a minimum of 2 hours.

The matrix material cannot be steam sterilized by ordinary means such as steam sterilization (121° C., 15 minutes, 2 bar) because the material would melt. This problem was overcome by a series of pre-rinses with a sterile solution, carried out within isolators, until a very low bioburden is reached. The pre-rinsed column matrix material is then bottled and steam treated at a lower temperature as described in Example 4 below.

The sterile, pyrogen-free matrix material is then activated by incubation with cyanogen-bromide solution as described in Example 5 below.

Once the column matrix material is activated, the antibodies are coupled to the column by incubation with the activated matrix (Example 5).

Alternatively, for simultaneous activation and coupling, the antibody solution is combined with 1,1'carbonyldiimidazole (CDI) in the reaction vessel and allowed to incubate overnight at room temperature (Example 5).

Once the coupling procedure is finished, the matrix material having antibodies coupled thereto is extensively washed and tested for cyanate ester, sterility, and pyrogenicity. The coupled matrix material is also tested for total bound protein, and binding activity of the coupled protein. The coupled matrix material is then filled under aseptic conditions into sterile, depyrogenated, silanized glass housings to form sterile and pyrogen-free protein-coupled columns.

Thus the present invention provides methods to produce sterile and pyrogen-free columns coupled to protein which retains its desired binding activity. The sterile and pyrogen-free columns are suitable for use with human subjects in need of the removal of predetermined substances from their blood. Moreover, the method is practical for producing the columns on a large scale, preferably at least about 40,000 columns per year or more.

The following experimental examples are offered by way of illustrating the invention, and are not meant to limit the scope of the invention.

EXAMPLE 1

Production and viral inactivation of anti-human Ig and anti-human LDL antibody solutions The production of immunized sheep plasma was carried out under Good Manufacturing Practices approved by the local government of Heidelberg, Germany. The flock of healthy male sheep was kept in a special paddock isolated from other animals. Their natural grass feed was supplemented by the provision of additional nutritional feed without animal meal. All sheep were examined on a routine basis by a qualified veterinary surgeon, who followed written procedures for care of the animals. The incoming new sheep were first placed in quarantine for a minimum of three weeks and tested serologically (antibody search for *Brucella melitensis*, Leptospira, *Listeria monocytogenes*, and Border Disease virus). An additional test for antibodies against Maedi Visna virus was done every six months for a total of three tests.

Polyclonal antisera directed against human immunoglobulin were raised by injecting sheep with a human IgG immunogen prepared from a pooled human plasma fraction of immunoglobulin (Gammagard S/D™, Baxter Hyland) together with complete Freund's adjuvant.

Polyclonal antisera directed against human LDL were raised by injecting sheep with an immunogen composed of complete Freund's adjuvant and affinity-chromotography purified LDL from the plasma of human subjects. The subjects who donated LDL were rigorously screened, and monitored after donation, for major blood born viruses. Moreover, the holding period between the collection of LDL and its first use was a minimum of 6 months. Thus, any donated LDL from subjects who tested positive for virus during this time could be rejected before release of product.

The animals received initial and booster injections of immunogen. Plasma was obtained from the immunized animals by routine plasmapheresis using a cell separator device equiped with sterile, pyrogen-free diposable tubing sets. The sheep plasma was anti-coagulated with ACD. The disposable tubing sets were primed with sterile, pyrogen-free sodium chloride solution. Plasma was collected via a closed tubing system in sterile, pyrogen-free transfer packs (Baxter/Fenwal) and immediately frozen at about −20° C. (range −18° C. to −30° C.). The plasma was stored frozen until the next processing step.

Alternatively, monoclonal antibodies could be raised against human immunoglobulin by first injecting mice with an appropriate antigen such as a human kappa or lambda light chain. Monoclonal antibodies against human LDL could be raised by first injecting mice with a purified preparation of LDL. The spleen cells of the immunized mice could then be fused with myeloma cells to form antibody-producing hybridomas (Köhler, G. and and Milstein, C., 1975 *Nature* 256:495–497).

In order to select for monoclonal antibodies to couple to a column useful for preparing a subject for a pig organ transplant, the secreted anti-human Ig monoclonal antibodies could be screened in a porcine endothelial cell ELISA-type assay as follows: (1) multiwell tissue culture plates would be prepared with a coating of porcine endothelial cells; (2) the porcine endothelial cells would be incubated with human immunoglobulin to allow human anti-pig antibodies to bind to the pig cells; (3) human immunoglobulin which does not bind to pig cells would be rinsed away; (4) conditioned media from individual monoclonal hybridomas would be incubated in the wells to allow monoclonal antibodies to bind to the human anti-pig antibodies, which in turn would be bound to the pig cells in the wells; (5) markers for the monoclonal antibodies would be added such as fluorescein-conjugated sheep anti-mouse antibodies; (6) the wells which fluoresced brightly would be considered positive for containing a monoclonal antibody which binds to human immunoglobulin, which in turn binds to pig cells.

Secreted anti-human LDL antibodies could be screened in an ELISA based on LDL-bound ELISA plates.

In this way, one or more appropriate monoclonal antibodies would be identified for large-scale production. These monoclonal antibodies could then be purified by affinity chromatography followed by ion-exchange chromatography, and then coupled to the column matrix material as described below.

Once an appropriate monoclonal antibody is identified and sequenced, it would then become possible to produce recombinant antibodies such as multiple- or single-chain antibodies. In another embodiment of the invention, these recombinant antibodies could be coupled to the column matrix material. Recombinant multiple-chain antibodies could be produced according to the methods described in U.S. Pat. No. : 4,816,397 (Boss, et al.; herein incorporated by reference). Recombinant single-chain antibodies could be produced according to the methods described in U.S. Pat. No. : 4,946,778 (Ladner, et al.; herein incorporated by reference).

When the antibodies are produced as monoclonals or by genetic engineering, it is possible to closely control their sterility. However, when the antibody to be coupled to the column is raised in an animal, it is especially important to assure that any viruses present in the animal serum are inactivated.

In the case of polyclonal antisera raised in sheep, described above, the following procedures were carried out under aseptic conditions using sterile and pyrogen-free instruments, plastic products, and solutions. The plasma pool was recalcified by addition of 1–10 µl $CaCl_2$ solution (1 mol/l) per ml of serum, and stirring at room temperature overnight. The plasma clot was then separated by centrifugation.

The animal serum was prepared for virus-inactivating heat treatment by mixing with a stabilizer consisting of saccharose (30% w/w) and ascorbic acid (5 mmol/l). The stabilized serum was then filled into empty bags, heated to at least 60° to about 62° C., and held at this temperature for at least 10 hours. The heat treated serum was filtered into empty bags through a 20 µm transfusion filter. The filled bags were aseptically sealed, labeled and stored at −20° C. (range −18°−−30°).

This viral inactivation process, as well as subsequent processes, were validated by spiking with three model viruses prior to each production step, and then assaying for any remaining infective virus. These 3 model viruses (human polio virus type 2, human adeno virus type 2, and ovine maedi visna virus) represented a range of human and animal viruses with different physicochemical properties. The maedi-visna virus of sheep is a lentivirus (retrovirus). The adenoviruses are large DNA viruses and, like other unenveloped viruses tend to be more resistant than enveloped viruses to physico-chemical inactivation. Poliovirus is a small RNA virus that is particularly resistant to many physico-chemical processes, including the use of low pH buffers, which are used at several steps below. In processes involving human blood products, a herpesvirus was spiked in replacement for the adenovirus. Specific inactivation studies in human blood products were also conducted for HIV.

As an extra level of precaution, two further viral inactivation processes can be employed, solvent/detergent treatment and virus filtration. Solvent/detergent treatment is intended for the inactivation of lipid-enveloped viruses. The pH of the product solution is first adjusted to pH 4.5. The solvent/detergents Tween®80 (0.3%), Triton®X-100 (1.0%), and Tri-N-Butylphosphate (0.3%) are then added to the product solution. After addition of solvent/detergent reagents, the mixture is stirred for a minimum of 1 hour at room temperature.

Virus filtration removes viruses by tangential flow filtration. The membrane used is Viresolve™180 from Millipore. The pore size of the membrane excludes molecules larger than 180 kD. The membrane is first rinsed with sterile water to remove storage solution. Then it is autoclaved for 60 minutes at 121° C. Prior to virus filtration the membrane is equilibrated with equilibration buffer. At first, 90% of the product solution volume is filtered by tangential flow filtration through the membrane. Following the initial filtration, a diafiltration is performed. The remaining 10% of the product solution is diluted with 1 volume part of equilibration buffer. This diafiltration step is performed 4 times. After the filtration is complete, the membrane is cleaned and tested for integrity by "CORR-Test".

After the virus inactivation step, the serum pool was again frozen as above. The next step in processing of the serum pool involves circulation over two glass columns known as the pre-column and the working column. In the case of anti-LDL serum, the pre-column contains Sepharose™ coupled to human Ig and human albumin, and the working column is coupled to human LDL. In the case of anti-human Ig serum, the pre-column contains Sepharose™ coupled to human albumin and the working column is coupled to human Ig.

EXAMPLE 2

Preparation of pre-column and working columns

All of the steps were conducted under aseptic conditions.

Pre-column for anti-LDL: Human serum albumin and IgIV (Gammagard®S/D, Baxter Hyland Division) were coupled to Sepharose™ essentially as described below.

Pre-column for anti-human Ig: Human serum albumin was coupled to Sepharose™ essentially as described below.

Working column for anti-LDL: LDL was obtained by affinity chromotography from the plasma of subjects as described above, and coupled to Sepharose™ as described below.

Working column for anti-human Ig: A preparation of pooled human immunoglobulin (Gammagard®S/D, Baxter, Hyland Division) was dissolved in buffer (140 g Gammagard®/100 ml buffer). The dissolved Gammagard™ was subjected to ultrafiltration to remove glycine, because it was found that glycine impairs the chromatographic separation of IgG from albumin. Gammagard® typically contains, per 10 g lyophilisate, 4500 mg glycine/100 ml. The goal was to reduce the glycine content to less than 960 mg/l, which required six ultrafiltration steps. For ultrafiltration, the Gammagard® was diluted with sterile buffer to 5000 ml, the solution was concentrated to 1000 ml, and the steps were repeated 5 more times. Then the Gammagard® solution was passed through a 0.2 μm sterilizing filter.

Human IgG was isolated from Gammagard® using two gradient steps of ion exchange chromatography (300 ml Q-Sepharose™ Fast Flow packed into a XK50/30 column; column height ca. 14 cm, diameter 5 cm; Pharmacia) at 2°–8° C. The purity of the isolated IgG was tested using SDS gel electrophoresis.

The next step was to couple the IgG to the column matrix material. However, it was discovered that TRIS and residual glycine in the purified IgG solution impaired the coupling of IgG to the column matrix material. To overcome this problem, an 11-step ultrafiltration procedure was devised to reduce the TRIS content to less than 211 μg/l and the glycine content to less than 35 μg/l. The volume of the IgG solution was brought to 5000 ml with pH 9 sterile sodium carbonate buffer. The solution was concentrated by ultrafiltration under constant stirring to 1000 ml, and the procedure was repeated 10 times. After the 10th step, the solution was reduced to 2000–2500 ml. The solution was then analyzed for protein, TRIS, and glycine content, and sterile filtered in an isolator. The solution was at pH 9 at this step.

Alternatively, a mix of human immunoglobulins such as IgG and IgM could be coupled to the sterile matrix.

The matrix material was sterilized, activated, and coupled to the appropriate protein solution as described below for preparation of the therapeutic columns. Results: At least 15 g (range 10–20 g) human IgG was coupled to 350 g (range 300–400 g) of matrix material in order to achieve a sufficient binding capacity for the working column.

EXAMPLE 3
Sterile purification of anti-human Ig antibodies

The pasteurized serum pool from Example 1 was thawed and circulated over two glass columns, one containing Sepharose CD4B coupled to albumin (pre-column) and the other containing Sepharose CL4B coupled to IgG (working column).

The serum loading and column washing process was carried out by a closed automated chromatographic system (BioPilot™ system, Pharmacia) in a class 100,000 clean room at an ambient temperature of 2°–8° C. The BioPilot™ system was under permanent bioburden control, CIP-runs (cleaning in place procedure) were done routinely, and during longer stand-times the pre- and working columns were filled with 0.1% sodium azide solution.

The connections from the system to containers of the sheep serum, the sterile buffers, and the sterile filters were made under aseptic conditions with specially designed disposable, sterile, and pyrogen-free plastic tubing sets.

At the beginning of each run, the serum can be diluted up to 5000 ml with sterile PBS buffer. The serum solution was then passed automatically over the pre-column, followed by automatic passage over the working column.

Once the desired antibodies had bound to the working column, and the undesired substances had flowed out of the column, the desired antibodies were eluted from the working column. Preferably, after 3000–8000 ml elution buffer had been passed, the collected eluate contained 70–100% of the antibodies originally loaded onto the columns.

Optimal results were achieved only after the preferred elution buffers were discovered. Laboratory experiments using various elution buffers are shown in Tables 1–3 below:

TABLE 1

Yield of eluted sheep antibody using different elution buffers

| buffer components | pH | osmolality [mOsm/kg] | eluted antibody [mg] | [%] |
|---|---|---|---|---|
| 0.10 M Sodium-Acetate/ 0.150 M NaCl/HCl (Baxter) | 2.8 | 387 | 14.99 | 100.0 |
| 0.20 M Glycine | 2.8 | 254 | 18.50 | 123.4 |
| 5 mM tri-Sodium-Citrate/ Citric acid | 2.2 | 211 | 24.37 | 162.6 |
| 5 mM mono-Sodium-Citrate/ Citric acid | 2.2 | 110 | 23.94 | 159.7 |
| 5 mM mono-Sodium-Citrate/ Citric acid | 2.8 | 26 | 19.23 | 128.3 |
| 5 mM Sodium-Acetate/Acetic acid | 2.8 | 537 | 23.57 | 157.2 |
| 5 mM Sodium-Propionate/ Propionic acid* | 2.8 | 1250 | 23.54 | 157.0 |

*Despite effective elution of antibodies, further analysis showed that the antibodies aggregated within a short period of time. For that reason, both buffers were excluded from further experiments.

The percentage yield was related to the amount of antibody eluted with Acetate buffer (Baxter) (100%).

TABLE 2

Stability of Isolated Antibody

| storage 2–8° C. (days) | Elution buffer | aggregates | Dimer | Monomer | Σ Mono/Dimer | fragments |
|---|---|---|---|---|---|---|
| 0 | Baxter-Acetate pH 2.8 | 5.4 | 10.4 | 82.1 | 92.5 | 2.1 |
|  | 5 mM Acetate/Ac. acid pH 2.8 | 2.6 | 6.8 | 87.1 | 93.9 | 3.5 |
|  | 5 mM mono-Sodium Citrate pH 2.2 | 1.4 | 5.7 | 90.9 | 96.6 | 2.1 |

TABLE 2-continued

Stability of Isolated Antibody

| storage 2–8° C. (days) | Elution buffer | aggregates | Dimer | Monomer | Σ Mono/Dimer | fragments |
|---|---|---|---|---|---|---|
| → | 5 mM mono-Sodium Citrate pH 2.8 | 1.1 | 2.1 | 93.9 | 96.0 | 2.8 |
|  | 5 mM mono-Sodium Citrate pH 3.0 | 2.3 | 6.0 | 89.0 | 95.0 | 2.7 |
| 6 | Baxter-Acetate pH 2.8 | 4.2 | 9.1 | 85.0 | 94.1 | 1.8 |
|  | 5 mM Acetate/Ac. acid pH 2.8 | 1.0 | 2.9 | 94.3 | 97.2 | 1.8 |
|  | 5 mM mono-Sodium Citrate pH 2.2 | 1.5 | 4.7 | 91.8 | 96.5 | 2.0 |
| → | 5 mM mono-Sodium Citrate pH 2.8 | 1.3 | 2.1 | 93.5 | 95.6 | 3.1 |
|  | 5 mM mono-Sodium Citrate pH 3.02 | 2.5 | 6.5 | 88.1 | 94.6 | 2.9 |
| 13 | Baxter-Acetate pH 2.8 | 6.1 | 10.0 | 80.5 | 90.5 | 3.4 |
|  | 5 mM Acetate/Ac. acid pH 2.8 | 2.1 | 4.4 | 91.2 | 95.6 | 2.3 |
|  | 5 mM mono-Sodium Citrate pH 2.2 | 5.2 | 5.1 | 87.3 | 92.4 | 2.4 |
| → | 5 mM mono-Sodium Citrate pH 2.8 | 1.2 | 2.3 | 93.1 | 95.4 | 3.4 |
|  | 5 mM mono-Sodium Citrate pH 3.0 | 2.8 | 7.5 | 86.3 | 93.8 | 3.3 |
| 20 | Baxter-Acetate pH 2.8 | 6.8 | 10.0 | 78.6 | 88.6 | 4.6 |
|  | 5 mM Acetate/Ac. acid pH 2.8 | 2.6 | 2.1 | 92.5 | 94.6 | 2.9 |
|  | 5 mM mono-Sodium Citrate pH 2.2 | 1.2 | 3.4 | 92.7 | 96.1 | 2.6 |
| → | 5 mM mono-Sodium Citrate pH 2.8 | 0.9 | 1.8 | 93.5 | 95.3 | 3.8 |
|  | 5 mM mono-Sodium Citrate pH 3.0 | 2.7 | 5.8 | 87.5 | 93.3 | 4.1 |
| 42 | Baxter-Acetate pH 2.8 | 5.2 | 9.5 | 79.9 | 89.4 | 5.5 |
|  | 5 mM Acetate/Ac. acid pH 2.8 | 1.7 | 2.2 | 91.7 | 93.9 | 4.5 |
|  | 5 mM mono-Sodium Citrate pH 2.2 | 1.0 | 2.9 | 91.5 | 94.4 | 4.6 |
| → | 5 mM mono-Sodium Citrate pH 2.8 | 0.9 | 2.6 | 92.8 | 95.4 | 3.7 |
|  | 5 mM mono-Sodium Citrate pH 3.0 | 6.2 | 7.7 | 82.8 | 90.5 | 3.3 |
| 56 | Baxter-Acetate pH 2.8 | 6.3 | 21.0 | 69.6 | 90.6 | 3.1 |
|  | 5 mM Acetate/Ac. acid pH 2.8 | 4.4 | 2.0 | 89.1 | 91.1 | 4.5 |
|  | 5 mM mono-Sodium Citrate pH 2.2 | 0.9 | 2.0 | 92.2 | 94.2 | 4.9 |
| → | 5 mM mono-Sodium Citrate pH 2.8 | 3.0 | 6.3 | 85.4 | 91.7 | 5.4 |
|  | 5 mM mono-Sodium Citrate pH 3.0 | 0.7 | 1.5 | 91.3 | 92.8 | 1.5 |
| 63 | Baxter-Acetate pH 2.8 | 2.9 | 9.2 | 76.5 | 85.7 | 11.4 |
|  | 5 mM Acetate/Ac. acid pH 2.8 | 0.3 | 1.2 | 91.6 | 92.8 | 7.0 |
|  | 5 mM mono-Sodium Citrate pH 2.2 | 6.0 | 3.0 | 85.5 | 88.5 | 5.6 |
| → | 5 mM mono-Sodium Citrate pH 2.8 | 2.2 | 1.9 | 93.4 | 95.3 | 2.5 |
|  | 5 mM mono-Sodium Citrate pH 3.0 | 3.7 | 6.0 | 72.8 | 78.8 | 17.6 |
| 70 | Baxter-Acetate pH 2.8 | 11.3 | 11.1 | 78.0 | 89.1 | 0.64 |
|  | 5 mM Acetate/Ac. acid pH 2.8 | 3.1 | 2.3 | 90.6 | 92.9 | 4.0 |
|  | 5 mM mono-Sodium Citrate pH 2.2 | 1.0 | 2.2 | 82.2 | 84.4 | 14.5 |
| → | 5 mM mono-Sodium Citrate pH 2.8 | 14.5 | 2.6 | 80.6 | 83.2 | 2.3 |
|  | 5 mM mono-Sodium Citrate pH 3.0 | 13.3 | 9.0 | 77.2 | 86.2 | 0.5 |
| 77 | Baxter-Acetate pH 2.8 | 2.7 | 11.0 | 75.2 | 86.2 | 11.1 |
|  | 5 mM Acetate/Ac. acid pH 2.8 | 0.7 | 1.4 | 93.2 | 94.6 | 4.7 |
|  | 5 mM mono-Sodium Citrate pH 2.2 | 0.5 | 2.1 | 90.5 | 92.6 | 6.9 |

TABLE 2-continued

Stability of Isolated Antibody

| storage 2–8° C. (days) | Elution buffer | aggregates | Dimer | Monomer | Σ Mono/Dimer | fragments |
|---|---|---|---|---|---|---|
| → | 5 mM mono-Sodium Citrate pH 2.8 | 0.8 | 1.9 | 91.5 | 93.4 | 5.9 |
|  | 5 mM mono-Sodium Citrate pH 3.0 | — | — | — | — | — | table 2:
Size distribution of sheep anti human IgG after storage at 2–8° C. in different elution buffers
Criteria for stored antibodies: Σ monomers
plus dimers ≧90%
AC. acid = Acetic acid

TABLE 3

Binding Capacity of
Ig-Therasorb ® Working Columns After Regeneration

| working column | binding capacity | |
|---|---|---|
|  | eluted antibody [mg/g Seph.] | [%] |
| column 1 | | |
| binding capacity of old material | 4.17 | 100 |
| after regeneration with Citrate buffer, pH 2.8 | 5.86 | 141 |
| after regeneration with Citrate buffer, pH 2.2 | 6.97 | 167 |
| column 2 | | |
| binding capacity of old material | 3.80 | 100 |
| after regeneration with Citrate buffer, pH 2.8 | 5.05 | 133 |
| after regeneration with Citrate buffer, pH 2.2 | 6.03 | 158 |

Results: Glycine buffer was found to be unsuitable because the glycine amino groups in the eluted antibody solution coupled to the activated matrix material in the subsequent coupling step. Therefore, with the glycine buffer, a time-consuming dialysis step was required to exchange the glycine for carbonate. The original acetate formulation was also unsuitable (0.10M sodium-acetate/0.150M NaCl/HCl, pH 2.8). Using either glycine buffer or the original acetate formulation, the amount of antibody eluted from the working column decreased over time, making the process relatively inefficient and costly. However, three buffer formulations were discovered that could efficiently elute the desired antibodies while retaining their binding capacity. Moreover, the presence of these new buffer components did not adversely affect subsequent production steps. The three preferred elution and storage buffers are:

(1) 5 mM mono-sodium citrate/10 mM citric acid, pH 2.8
(2) 5 mM mono-sodium citrate/63 mM citric acid, pH 2.2, which was found to be suitable for regeneration of working columns, but less suitable for long-term antibody storage.
(3) 5 mM acetate/acetic acid, pH 2.8

The stability of stored antibodies was assessed by the amount of intact monomers and dimers as compared with fragments. After a storage period of 77 days at 2°–8° C., the content of monomers and dimers in buffer (1) was 93% compared to 86% in the previous acetate formulation (0.10M sodium acetate/0.150M NaCl/HCl, pH 2.8).

The binding capacity of used columns was greatly improved by 33%–67% through regeneration with either buffer (1) or (2) above.

During the elution procedure, eluted antibodies were passed through sterilizing filters (0.2 μM) on-line and collected into disposable, sterile, and pyrogen-free receiving bags and stored at 2°–8° C.

In order to concentrate the antibody solutions, an ultra-filtration step was carried out in a class 100,000 clean room with a 10,000 kD membrane (Omega series, low binding polyethersulfone, Filtron Technology Corporation). Typically, the antibody solution was concentrated about 20–80 fold, or from about 50–200 liters down to about 2.5 liters. Samples of the processed antibodies were taken under aseptic conditions for in-process monitoring after the untra-filtration step.

At this point, the concentrated eluate contained about 74–97% of the antibodies originally bound to the column.

EXAMPLE 4

Preparation of sterile, pyrogen free column matrix material

The column matrix material was rendered sterile and pyrogen-free by a series of pre-rinses, followed by steam sterilization. The procedure was carried out inside a sterilized isolator.

Approximately two days before the start of this procedure, an agarose bulk material (Sepharose™CL4B) was filled aseptically into a sterile and pyrogen-free 5 liter beaker for settling by gravity overnight. On the second day, the volume of the Sepharose™ was checked for a minimum of 2100 ml settled gel (=6 bottles @ 350 ml) per one 5 liter beaker. The Sepharose™ volume was regulated aseptically, and allowed to settle again if necessary.

Working within the isolator, each batch of Sepharose™ was rinsed with a total volume of minimum 21 liters of sterile and pyrogen-free water, in steps of 4500 ml each. Between each step, the Sepharose™ was completely dried by vacuum. The final rinsed suspension was then filled into 500 ml bottles and closed with rubber stoppers.

Figure 1B:
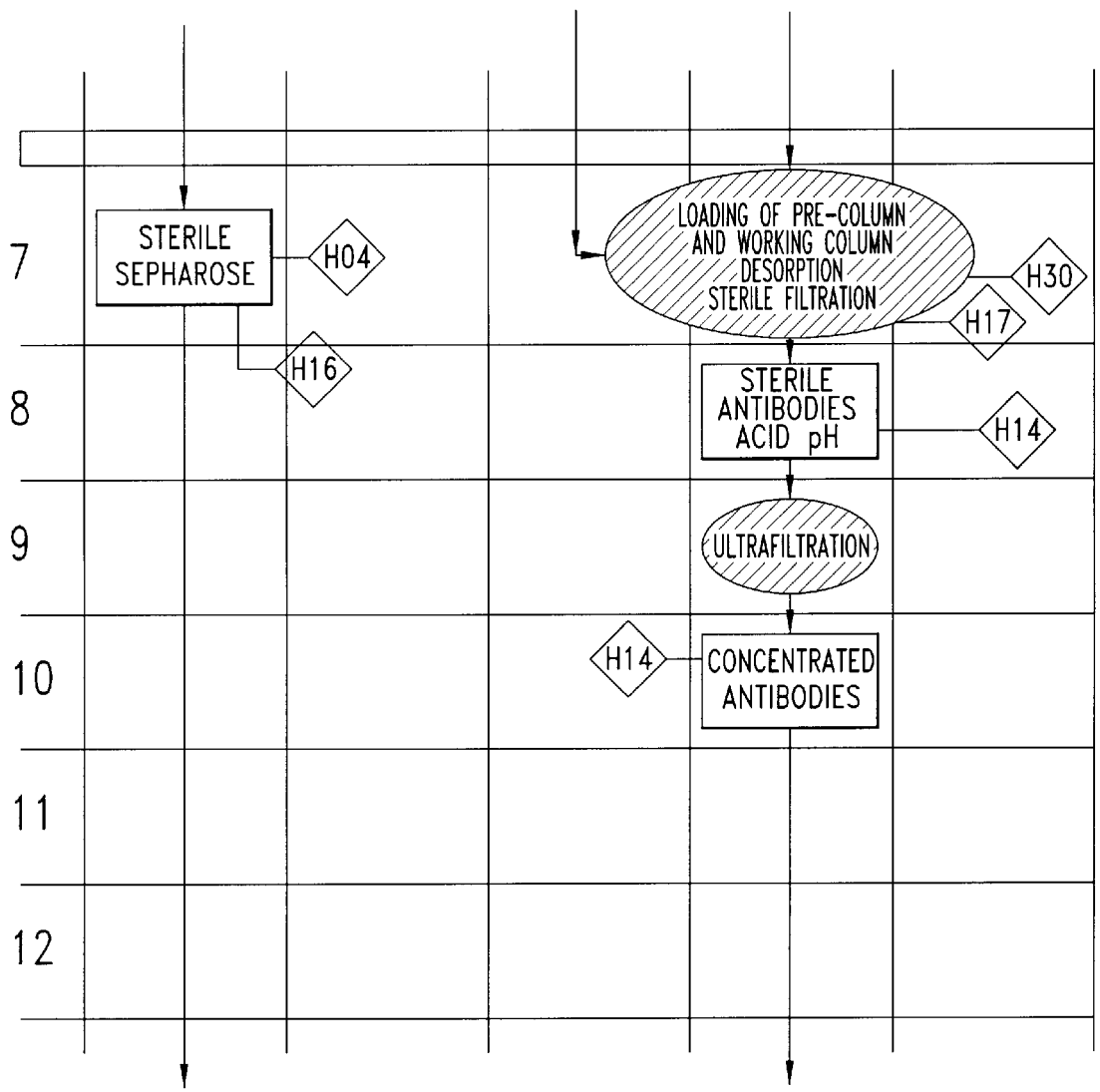
Figure 1C:
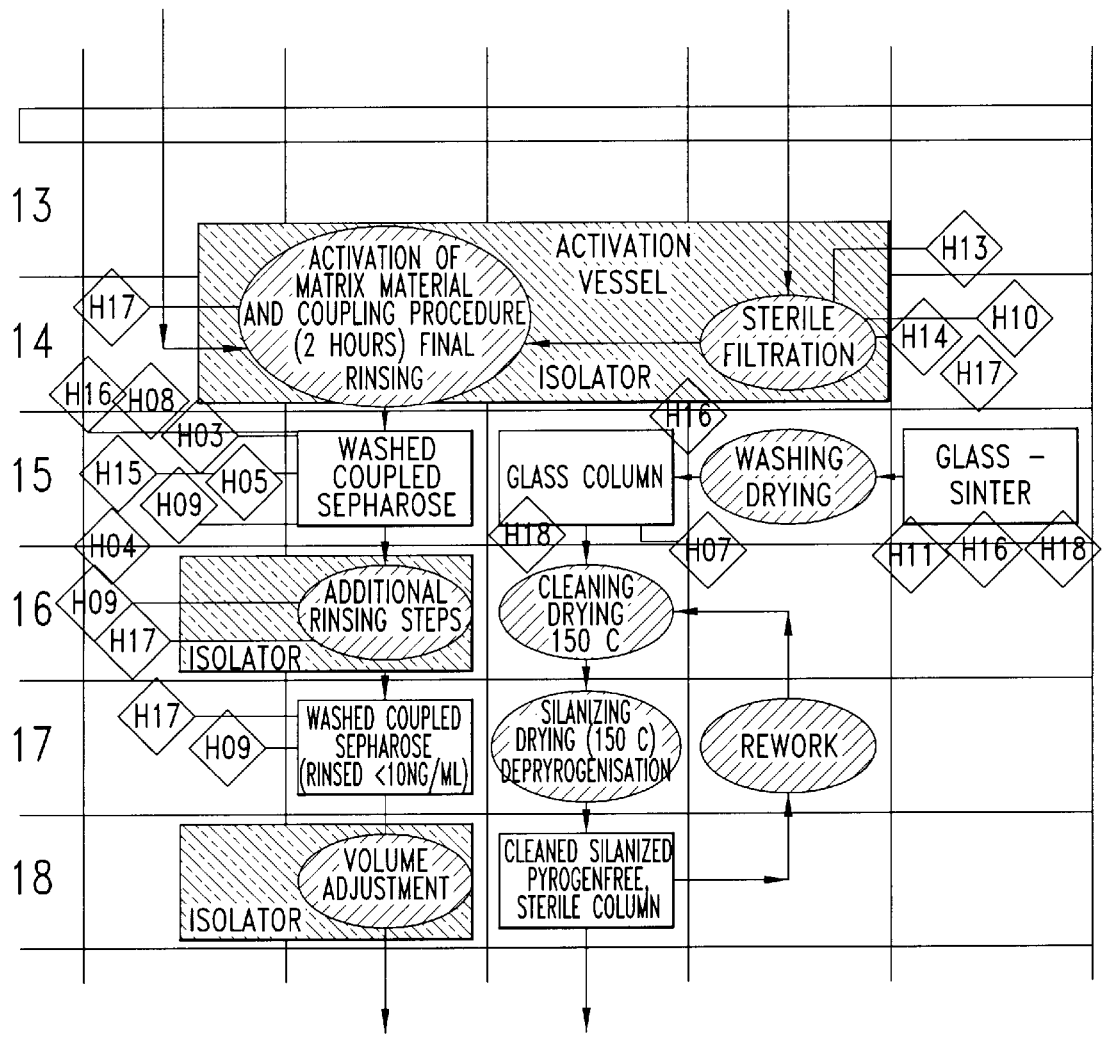
Figure 1D:
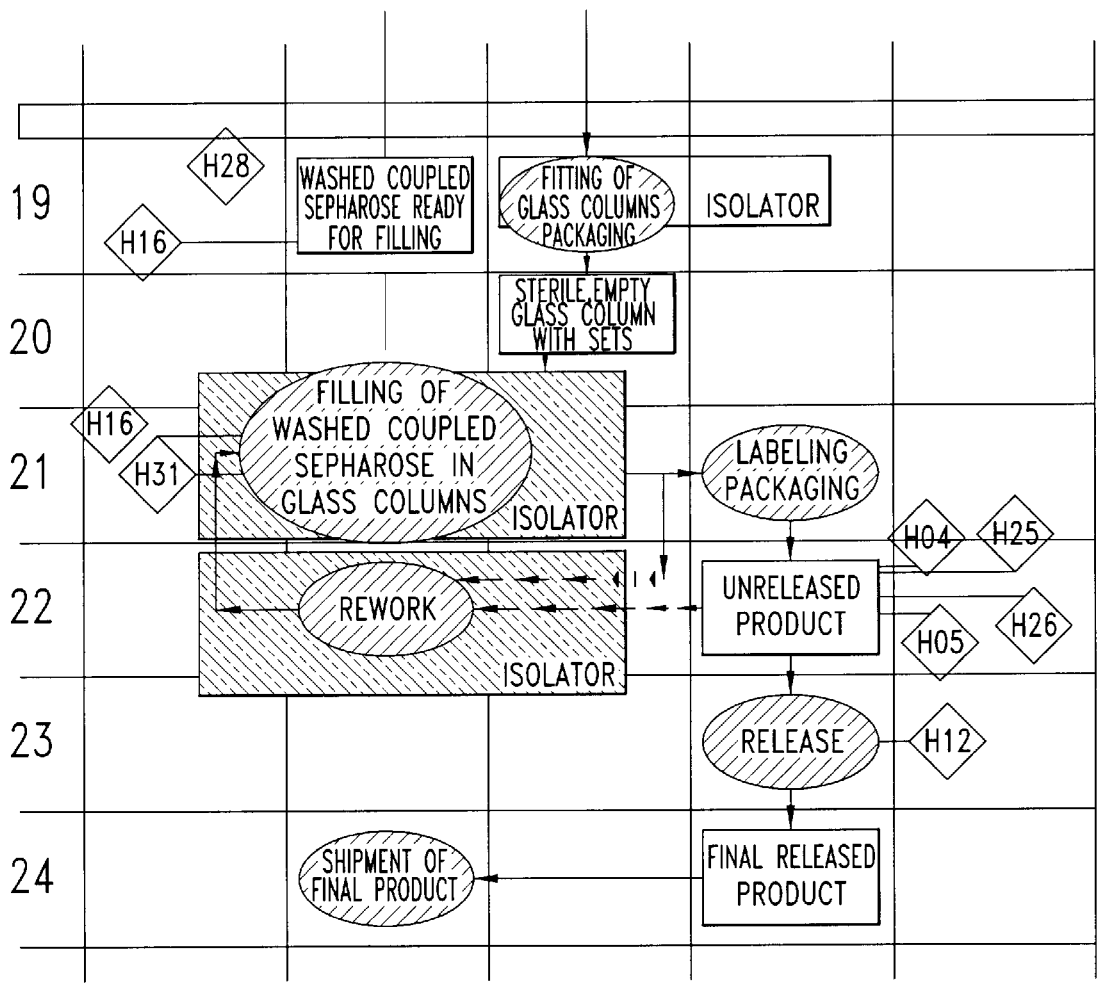

Samples were taken for bioburden determination. Bioburden testing was conducted at several points in the production process at H30, FIGS. 1(a)–1(e). Bioburden testing was required to show no enteric bacteria, no *Pseudomonas aeruginosa*, and no *Staphylococcus aureus*; an alert limit of 1 aerobe growing bacterium/g or ml of sample was set. The bottles were evacuated under aseptic conditions using a manual vacuum pump, and closed tightly with metal caps.

The bottles of rinsed Sepharose™ were then steam sterilized within 72 hours after the above rinsing step. The steam sterilization was conducted using a validated steam autoclave at 115° C. for a minimum of 20 minutes at <2 bar. The cycle time was regulated automatically to reach an $F_0$ value of 6. After steam sterilization, samples were taken for bioburden determination and testing for pyrogenicity. The bioburden test was required to show a maximum of 1 colony-growing organism/100 ml. The pyrogenicity test (Limulus-amoebocyte-lysate test) was based on the ability of endotoxins to cause egg-white gelling by an amoebocyte extract. The Lowry eggwhite test then was used to quantitate the endotoxin amount calorimetrically at 660 nm. The pyrogen content was required to be below 0.25 EU/ml.

EXAMPLE 5

Activation of matrix material and coupling of antibodies

This procedure and other procedures identified above and in FIG. 1 were carried out inside a sterilized isolator. One of the main difficulties is using isolators for aseptic work is the process of sterilizing the inside of the isolator itself before beginning the aseptic procedure. A vapor generator (La Calhene, France), heats peracetic acid (PAA) to form a vapor, and thereby fume sterilizes the isolator. This method is dry but slow-acting, due to lower chemical and water activity and vapor/air mixing problems. Fortuitously, it was discovered that a vapor nebulized mist could simplify the sterilization of the isolator by reducing the time and operator effort required. In the method of the present invention, the liquid sterilant was nebulized into the isolator in the smallest amount necessary to provide a saturated vapor and a surface condensation. During the introduction and exposure, the sterilant was circulated within the isolator. The nebulizer operated by breaking up liquid in a container through input of energy at ultrasonic frequencies. The nebulizer used was Ultra Neb™ 99 (DE VILBISS). The container of the nebulizer was filled with 200–210 ml of peracetic acid, and the tubing of the nebulizer was connected to the entrance at the backside of the isolator. The ventilator was installed inside the isolator at the clutch. The isolator was then loaded with the materials required for the next step according to a validated loading pattern. The air out tube was connected to the used air system. The nebulization process was begun, with a pressure inside the isolator of not more than 1 mm Hg. The nebulization was stopped when the PAA content of the nebulizer was reduced to 160 ml (nebulization uptake of 40–50 ml). This was followed by a holding time of at least 10 minutes. After the holding period, the isolator was flushed by switching on the ventilator of the isolator to isolator overpressure (approximately 4–5 mm Hg) and opening the outlet vent. For each individual isolator, a minimum flushing period was validated (typically a minimum of 80–110 minutes).

A stainless steel activation vessel was used to activate 1800 ml Sepharose™ CL4B in one batch within an isolator. The activation vessel had to be sterilized prior to use. At first, the stainless steel vessel was heat sterilized a 250° C.–280° C. for a minimum of 2 hours. However, this treatment created stresses between the scinter and the body of the activation vessel, which led to loose or thin spots between the scinter and the bottom. From this treatment, the material of the activation vessel wore out quickly. Gas nebulization sterilization was used instead.

An isolator was installed in a class 100,000 clean room. All materials and labware were installed in the isolator, the inside of which was then sterilized by the ultrasonic nebulization process described above. A waste container filled with calcium hypochlorite for CnBr inactivation was installed outside the isolator. Pall™ sterile filter units were sterilized and installed on the isolator. One filter was used for filtration of sterile pyrogen-free water into the isolator, and the other was used for removal of waste liquids into the outside waste container.

Working inside the isolator, the Sepharose™ was rinsed three times with sterile, pyrogen-free water, and then rinsed and resuspended in 60% acetone/water. Next, the Sepharose* was activated with CnBr and triethylamine (TEA) solution. CNBr:14–15 g cyanogen bromide per 96 ml acetone. For activation within the stainless steel vessel, 1800 ml was required. TEA: 30 ml triethylamine (analytical grade, Merck) in 66.2 ml of 87% acetone. The Sepharose™/ acetone/water slurry was cooled to −18° C., and the CNBr solution (about 580–650 ml) was added in a continuous flow over 1 minute. Then the TEA solution (about 580–650 ml) was added in a continuous flow over 2 minutes. The temperature of −10° C. was reached when the exothermic reaction was finished (approximately 45 seconds after finishing the TEA addition). One minute after the TEA addition, the acetone/HCl solution was added. Acetone/HCl: 392 ml sterile, pyrogen-free water, 16.3 ml 5N HCl, 408 ml acetone. Several bottles of Sepharose™ were activated one at a time in this fashion. Activated Sepharose™ was used for coupling within 3 hours, preferably as soon as possible.

A cyanate ester determination was performed on the activated Sepharose™ using the Spectroquant® test kit (Merck) before adding the concentrated antibodies to test the efficiency of the chemical activation.

After activation, the Sepharose™ was quickly rinsed in the activation vessel five times in sterile, pyrogen-free water. This step had to be performed quickly in order to avoid hydrolysis of active groups. The sterile filtered antibody solution was then transferred into the activation vessel and stirred for 2 hours. After 2 hours the Sepharose™ suspension was then rinsed 2 times by alternating solutions of pH 2.8 (range 2.2–3.0) and PBS. The Sepharose™ was gently resuspended in PBS and repeatedly rinsed using a total of 60 (range 50–200 liters) of 0.9% NaCl per one activation vessel batch (about 1800 ml Sepharose™). The antibody coupled Sepharose™ bulk was then filled into sterile bottles and capped with a metal cap. The bottles were stored at 2°–8° C. until the next production step. It was found that the bottles could be stored up to 12 weeks.

The used filters were tested for integrity. [Filter integrity tests were performed several times in the production process, namely at H17 and H31, FIG. 1]. After finishing the activation and coupling, the suspension supernatant was subjected to another cyanide test for residual cyanide.

Next, additional rinsing with sterile 0.9% NaCl was carried out to reach an uncoupled protein content in the supernatant below 10 ng per ml The amounts of bound and unbound protein were determined by standard methods. Using the above procedures, it was possible to obtain at least 50–100 g of antibody coupled to 1800 ml Sepharose™ (range 1800–2000 ml).

Each batch was assayed for protein content using the BCA (bicinchoninic acid) reagent and absorption at 562 nm (Smith, et al., *Anal Biochemie* 1985). An alternative method for activating and coupling is based on the use of 1,1'-carbonyldiimidazole (CDI). This method will work for matrix materials such as cellulose, agarose, or polystyrene that have hydroxy or carboxyl groups to which the antibodies can be coupled. A single reaction vessel is used for the simultaneous activation of the matrix material and the coupling of the antibodies to the activated material. The reaction buffer is 0.1 mol/l $NaHCO_3$ pH 8.1–8.2. CDI is added to the reaction vessel at a final concentration of 6.2 mg/ml (38.2 mmol/l). The protein solution is added to concentrations of between 400 µg/ml to 1000 µg/ml. The whole reaction is carried out at room temperature, including the incubation of matrix material with CDI and antibody solution overnight for about 12–20 hours, preferably 15 hours. Possible residual active groups are then saturated by washing the antibody-coupled matrix material with 0.1 mol/l ethanolamine in 0.1 mol/l NaHCO$_3$ pH 8.0. Finally, rinsing with 0.1 mol/l NaOAc-buffer pH 4.0 is used to destroy any residual free active groups. The amount of antibody coupled to the matrix material is determined using the BCA protein assay. The yield of antibody coupled to the matrix material depends on the ratio of protein to matrix material in the reaction mixture. With a low ratio of antibody to matrix material, up to 100% of the antibody can be coupled. Increasing the ratio of antibody to matrix material leads to greater absolute amounts of antibody coupled, until a plateau is reached. After this point, increasing the ratio of antibody to matrix material in the reaction mixture leads to lesser percentages of antibody coupled, probably due to saturation of the matrix material surface area with protein.

EXAMPLE 6

Finishing of final product

Glass column housings with glass sinter were cleaned, dryed, silanized, and depyrogenated, and then fitted with their connection sets inside a sterilized isolator.

The washed, protein-coupled Sepharose™ was filled into the glass column housings inside the sterilized isolator. Samples were taken for heavy metal analysis, particle analysis, pyrogenicity, and sterility tests.

EXAMPLE 7

Monoclonal antibodies as alternatives to polyclonal antibodies bound to columns

It was the objective of the following experiments to demonstrate reduction of the immunoglobulin classes IgG, IgM and IgA in human plasma by using an immunoadsorption device consisting of monoclonal antibodies covalently coupled to a solid support. Additionally, removal of all four subclasses of human IgG was to be assessed.

Materials

Sepharose® CL-4B, Pharmacia

Ultrafree®-CL Filters (nominal molecular weight limit: 10 kD), Millipore®

Mobicol® empty columns with 10 μm membrane, MoBitec®

Anti human κ light chain monoclonal antibody (isotype IgG$_1$, Maus), Biozol®

Anti human λ light chain monoclonal antibody (isotype IgG$_1$, Maus), Biozol®

IgG subclasses kit, ICN

Antibody IgG, IgM, IgA, incl. buffer and diluent, Beckman

Phosphate buffered saline (PBS) (pH 7.2), Baxter

Acetate buffer (pH 2.8), Baxter

Glycine (pH 2.8), Baxter

Methods

Binding of human immunoglobulins of classes IgG (including subclasses 1–4), IgA and IgM as well as xeno-reactive antibodies (human anti porcine cells IgG and IgM) was achieved with a relatively simple mixture of monoclonal antibodies specific to human immunoglobulin κ light chains and human immunoglobulin λ light chains. The experiments were carried out in a small scale with 300 μl of antibody coupled Sepharose®.

Coupling of antibodies to Sepharose® CL-4B

A mixture of the two types of monoclonal antibodies (5 mg each) was concentrated by centrifugation in Ultrafree®-CL Filters (2000 g, 8° C.) to a concentration of 2 mg/ml. Before coupling, pH of the antibody solution was adjusted to 9.0 with sodium hydrogen carbonate buffer, pH 11. Activation of Sepharose® CL-4B with cyanogenbromide was performed as described above. Afterwards the antibodies were coupled to Sepharose® overnight at 2°–8° C. For coupling, 10 mg antibodies per 250 mg Sepharose® were used. After coupling, the Sepharose® was washed five times with acetate buffer, pH 2.8, and PBS buffer, pH 7.2, alternately to rinse off unbound antibodies.

Plasma processing

Following transfer of the antibody coupled Sepharose® into an empty Mobicol® column (66.5 mm×105 mm, volume: 0.30 ml packed medium) human plasma was loaded onto it. Plasma was incubated for 30 min. Afterwards, the plasma was rinsed off with a 10-fold column volume of PBS (3 ml).

Quantification of immunoglobulins

Quantification of immunoglobulins (IgG 1-4, IgA, IgM) in both untreated and processed plasma was performed by means of radial immunodiffusion (RID).

Quantification of xenoreactive antibodies

Reduction of xenoreactive antibodies was measured by means of a Porcine Endothelial Cell (PEC) immunoassay (ELISA) as described in Platt, J. L., et al. *Transplantation* 49:1000–1001, 1990. Briefly, porcine aortic endothelial cells were isolated and cultured in Dulbecco's modified Eagle's medium containing 20% fetal calf serum (Ryan, U.S., et al., *J Tissue Cult Methods* 1986; 3). The cells were grown to confluence in 96-well microtiter plates (Nunc™). Cells in the wells were rinsed in PBS and fixed in 200 μl of cold glutaraldehyde solution (0.1%) at 4° C. for 5 minutes, followed by washing in Hank's balanced salt solution (HH). Non-specific binding sites on the cells were blocked by incubating the cells in HH containing 1% bovine serum albumin (BSA) for 45–60 minutes at room temperature. Positive control sera were pooled human serum (PHS). Fifty μl of the control and test sera were added to the wells and incubated for 1 hour at 4° C. (for the IgM ELISA) or at 37° C. (for the IgG ELISA), followed by 3 rinses in HH. Fifty μl of the secondary antibody was added to each well and incubated at room temperature for 1 hour. The secondary antibody for the IgM ELISA was goat anti-human IgM conjugated to alkaline phosphatase; the secondary antibody for the IgG ELISA was goat anti-human IgG similarly conjugated. After washing, the marker reaction was developed in diethanolamine (0.1M with 0.5×10$^3$M MgCl$_2$) with phosphatase substrate (1 mg/ml p-nitrophenyl phosphate). The developer/substrate was added at 100 μl/well, and the plates were incubated in the dark at room temperature for about 30 minutes, or until the positive control read 1–1.5 absorbance at 405 nm. The plates were read at 405 nm on a standard ELISA plate reader.

Results

TABLE 4

Quantification of immunoglobulins

| parameter | immunoapheresis | amount in plasma [mg] | reduction [%] |
|---|---|---|---|
| IgG | before IA | 5.28 | 0.0 |
|  | after IA | 4.06 | 23.1 |
| IgA | before IA | 0.90 | 0.0 |
|  | after IA | 0.76 | 15.5 |
| IgM | before IA | 0.65 | 0.0 |
|  | after IA | 0.49 | 24.6 |
| IgG 1 | before IA | 3.46 | 0.0 |
|  | after IA | 2.50 | 27.7 |
| IgG 2 | before IA | 2.03 | 0.0 |
|  | after IA | 1.44 | 29.1 |
| IgG 3 | before IA | 0.32 | 0.0 |
|  | after IA | 0.22 | 31.3 |

TABLE 4-continued

Quantification of immunoglobulins

| parameter | immunoapheresis | amount in plasma [mg] | reduction [%] |
|---|---|---|---|
| IgG 4 | before IA | 0.26 | 0.0 |
|  | after IA | 0.18 | 30.8 |

Quantification was performed by radialimmunodiffusion (RID). Employed standard sera were standardized according to World Health Organization.
Plasma volume processed: 500 µl
Volume of Sepharose ®: 300 µl
Time of plasma processing: 30 min As shown in Table 4, all immunoglobulin classes and all IgG subclasses (1–4) were reduced by coupled monoclonal antibodies.

TABLE 5

Quantification of xenoreactive antibodies

| parameter | immunoapheresis | reduction [%] |
|---|---|---|
| human anti porcine IgG | before IA | 0.0 |
|  | after IA | 9.7 |
| human anti porcine IgM | before IA | 0.0 |
|  | after IA | not detectable |

Plasma volume processed: 500 µl
Volume of Sepharose ®: 300 µl
Time of plasma processing: 30 min Anti porcine IgG was reduced by about 10%. Reduction of anti porcine IgM was not detectable.

Discussion

It was shown that it is possible to reduce immunoglobulins in human plasma not only by means of polyclonal but also by monoclonal antibodies coupled to a solid support. To achieve a reduction of all immunoglobulins in the plasma, irrespective of their type and specificity, monoclonal antibodies were chosen which were expected to recognize and bind them all. The two mouse antibodies (isotype $IgG_1$) employed were specific to human immunoglobulin κ light chains and human immunoglobulin λ light chains, respectively. Monoclonal antibodies of other epitope specificities or isotypes, or recombinant antibodies could have been chosen as well.

The results show clearly, that all four IgG subclasses were reduced by the monoclonal antibody column (table 4). IgG subclasses 1,2, 3 and 4 were each lowered by about 30%. As obvious from table 5, reduction of xenoreactive antibodies could be determined only for IgG but not for IgM, because the immunoassay for determination of IgM is less sensitive than for IgG.

The relatively low reduction of immunoglobulins was not surprising, since the experiment was done on a small, analytical scale, i.e. with a small antibody column (300 µl Sepharose®), and only one plasma cycle was performed. For clinical purposes, larger monoclonal antibody columns and performances of several plasma processing cycles should lead to a satisfactory lowering of immunoglobulins and of the desired antibodies.

What is claimed is:

1. A method for producing a sterile and pyrogen-free column containing a matrix material having a protein coupled thereto, said column being useful for removing a predetermined substance from the blood of a human subject, said method comprising;

providing a purified solution of protein which binds to said predetermined substance in human blood, said solution being sterile and pathogen-free, providing a sterile and pyrogen-free matrix material which is chemically activated, wherein said matrix material is rendered sterile and pyrogen-free by a procedure comprising the steps of:

(a) rinsing said matrix material, under aseptic conditions, with sterile and pyrogen-free water until a bioburden test indicates the presence of zero enteric bacteria, zero *Pseudomonas aeruginosa*, zero *Staphylococcus aureus*, and less than 1 aerobe growing bacterium/g, and (b) steam treating said matrix material under conditions which yield a value of $F_0=6$, contacting under aseptic conditions said activated matrix material with said solution of protein, thereby effecting the coupling of said protein to said matrix material, and packing under aseptic conditions said matrix material having said protein coupled thereto into sterile and pyrogen-free housing in the form of a column to produce said sterile and pyrogen-free column containing matrix material having a protein coupled thereto.

2. The method of claim 1 wherein said solution of protein is selected from the group consisting of *Staphylococcus aureus* Protein A, Streptococcus Protein G, anti-human immunoglobulin antibodies, and anti-human low-density-lipoprotein (anti-LDL) antibodies.

3. The method of claim 1 wherein said predetermined substance to be removed from human blood is selected from the group consisting of immunoglobulin G (IgG), immunoglobulin M (IgM), immunoglobulin A (IgA), immunoglobulin E (IgE), low-density-lipoprotein (LDL), and lipoprotein a (Lp(a)).

4. The method of claim 1 wherein said solution of protein comprises antibodies, said antibodies being selected from the group consisting of polyclonal antibodies and monoclonal antibodies.

5. The method of claim 1 wherein said column matrix material is selected from the group consisting of beads, fibers, and membranes.

6. The method of claim 1 wherein said column matrix material is selected from the group consisting of glass, carbohydrates, polymethacrylates and polyamides.

7. The method of claim 6 wherein said column matrix material is an agarose.

8. The method of claim 1 wherein said solution of protein is derived from animal serum which is rendered pathogen-free by the steps comprising;

(a) adding to said serum a stabilizer comprising a carbohydrate and an anti-oxidant, thereby forming a stabilized serum mixture, (b) heating said stabilized serum mixture to a temperature range of from 60° C. to about 62° C., (c) maintaining said temperature range for at least 10 hours, and (d) filtering said stabilized serum mixture through a 20 µm filter into a sterile and pyrogen free container.

9. The method of claim 8 wherein said carbohydrate is saccharose at a concentration of about 30% w/w, and said anti-oxidant is ascorbic acid at a concentration of about 5 mmol/l.

10. The method of claim 1 wherein said solution of protein comprises anti-human low-density liproprotein (LDL) antibodies, and wherein said solution of protein is purified by the steps comprising;

(a) providing a sterile and pyrogen-free first column containing a first matrix material having human albumin and human immunoglobulin coupled thereto, (b) passing said protein solution over said first column under aseptic conditions, thereby removing any non-desired substances which bind to said first matrix material, (c) providing a sterile and pyrogen-free second column containing a second matrix material having human LDL coupled thereto, (d) passing said protein solution from step (b) over said second column under aseptic conditions, thereby effecting the binding of said anti-human LDL antibodies to said second matrix material, and (e) eluting said anti-human LDL antibodies with an acidic buffer.

11. The method of claim 1 wherein said solution of protein comprises anti-human immunoglobulin (Ig) antibodies, and wherein said solution of protein is purified by the steps comprising;

(a) providing a sterile and pyrogen-free first column containing a first matrix material having human albumin coupled thereto, (b) passing said protein solution over said first column, thereby removing any non-desired substances which bind to said first matrix material, (c) providing a sterile and pyrogen-free second column containing a second matrix material having human Ig coupled thereto, (d) passing said protein solution from step (b) over said second column, thereby effecting the binding of said anti-human Ig antibodies to said second matrix material, and (e) eluting said anti-human Ig antibodies with an acidic buffer.

12. The method of either claim 10 or claim 11 wherein said acidic buffer is selected from the group consisting of:

5 mM mono-sodium citrate/10 mM citric acid, pH 2.8, and 5 mM mono-sodium citrate/63 mM citric acid, pH 2.2.

13. The method of either claim 10 or 11 wherein said acidic buffer consists of 5 mM acetate/acetic acid, pH 2.8.

14. The method of claim 1 wherein step (b) is conducted at 115° C. at less than 2 bar.

15. The method of claim 1 wherein said sterile and pyrogen-free matrix is activated under aseptic conditions by the steps comprising;

(a) providing a sterile and pyrogen-free activation vessel, (b) suspending said matrix in acetone in said activation vessel to form a matrix/acetone solution, (c) cooling said matrix/acetone solution to −18° C., (d) adding a CnBr solution, (e) adding a triethylamine solution, thereby causing a temperature of 10° C. to be reached in the activation vessel, and (f) adding an acetone/HCl solution, thereby terminating the activation process, to obtain said activated, sterile and pyrogen-free matrix in the activation vessel.

16. The method of claim 15 wherein said contacting step to couple said protein to said matrix is conducted under aseptic conditions by the steps comprising;

(a) adding said sterile and pathogen-free solution of protein to said activation vessel containing said activated, sterile and pyrogen-free matrix from step (f) to form a slurry, (b) stirring said slurry for about 2 hours, (c) rinsing said slurry with alternating acidic and neutral solutions, (d) rinsing said slurry with at least 50 liters of phosphate-buffered saline (PBS) per about 1800 ml of slurry, and (e) resuspending said slurry in PBS.

17. The method of claim 1 wherein said sterile and pyrogen-free matrix material is activated and contacted with said solution of protein under aseptic conditions by the steps comprising;

(a) providing a sterile and pyrogen-free activation vessel, (b) combining in said activation vessel said sterile and pyrogen-free matrix material with 1,1'-carbonyldiimidazole (CDI) and with said protein solution, (c) incubating said matrix material with said CDI and said protein solution at about 19°–24° C. for about 12 to about 20 hours, thereby effecting the coupling of said protein to said matrix material, (d) washing said matrix material with 0.1 mol/l ethanolamine in 0.1 mol/l NaHCO$_3$ pH 8.0, thereby saturating residual active groups on said matrix material, and (e) adding to said matrix material 0.1 mol/l NaOAc buffer at pH 4.0, thereby destroying residual free active groups on said matrix material having said protein coupled thereto.

18. The method of claim 17 wherein in step (b) said CDI is combined at a final concentration of about 38.2 mmol/l in a reaction buffer comprising 0.1 mol/l NaHCO$_3$, at pH 8.1–8.2, and said protein solution is combined at a concentration of 400–1000 µg/ml.

19. The method of claim 4, wherein said antibodies are recombinant antibodies produced by genetic engineering.

20. A sterile and pyrogen-free column containing sterile and pyrogen-free matrix material coupled to protein produced by the method of claim 1.

* * * * *